United States Patent [19]

Essenpreis et al.

[11] Patent Number: 5,692,504

[45] Date of Patent: Dec. 2, 1997

[54] METHOD AND APPARATUS FOR THE ANALYSIS OF GLUCOSE IN A BIOLOGICAL MATRIX

[75] Inventors: Matthias Essenpreis, Gauting; Dirk Boecker, Heidelberg; Heinz-Michael Hein, Seeheim-Jugenheim; Hans-Peter Haar, Wiesloch, all of Germany

[73] Assignee: Boehringer Mannheim GmbH, Mannheim, Germany

[21] Appl. No.: 592,303

[22] PCT Filed: Oct. 29, 1994

[86] PCT No.: PCT/DE94/01290

§ 371 Date: Feb. 9, 1996

§ 102(e) Date: Feb. 9, 1996

[87] PCT Pub. No.: WO95/12348

PCT Pub. Date: May 11, 1995

[30] Foreign Application Priority Data

Nov. 4, 1993 [DE] Germany ............ 43 37 570.7

[51] Int. Cl.[6] ........................................... A61B 5/000
[52] U.S. Cl. ......................... 128/633; 128/664; 356/39
[58] Field of Search ....................... 128/633, 664–667; 356/39–41

[56] References Cited

U.S. PATENT DOCUMENTS

| | | | |
|---|---|---|---|
| 4,972,331 | 11/1990 | Chance | 128/633 |
| 5,028,787 | 7/1991 | Rosenthal et al. | 250/341 |
| 5,057,695 | 10/1991 | Hirao et al. | 250/575 |
| 5,119,815 | 6/1992 | Chance | 128/633 |
| 5,119,819 | 6/1992 | Thomas et al. | 128/660 |
| 5,122,974 | 6/1992 | Chance | 364/550 |
| 5,167,230 | 12/1992 | Chance | 128/633 |
| 5,178,142 | 1/1993 | Harjunmaa et al. | 128/633 |
| 5,179,951 | 1/1993 | Knudson | 128/633 |
| 5,187,672 | 2/1993 | Chance et al. | 364/550 |
| 5,551,422 | 9/1996 | Simonsen et al. | |

FOREIGN PATENT DOCUMENTS

| | | |
|---|---|---|
| 0 074 428 | 3/1983 | European Pat. Off. . |
| 0 160 768 | 11/1985 | European Pat. Off. . |
| 0 286 142 | 4/1987 | European Pat. Off. . |
| 0 473 241 | 8/1987 | European Pat. Off. . |
| 0 353 619 | 7/1988 | European Pat. Off. . |
| 0 426 358 | 5/1991 | European Pat. Off. . |
| 40 31 320 | 4/1992 | Germany . |
| 0426358 | 8/1991 | Rep. of Korea ............... A61B 5/00 |

OTHER PUBLICATIONS

"Proceedings of Photon Migration and Imaging in Random Media and Tissues", Progress in Biomedical Optics, SPIE, vol. 1888, Jan. 1993, pp.248–257.

(List continued on next page.)

*Primary Examiner*—Jennifer Bahr
*Assistant Examiner*—Bryan K. Yarnell
*Attorney, Agent, or Firm*—Nikaido, Marmelstein, Murray & Oram LLP

[57] ABSTRACT

Method and apparatus for the analytical determination of glucose concentration in a biological matrix, wherein in a detection step light from a light emitter is irradiated into the biological matrix as primary light via a boundary surface of the biological matrix and light emerging from the the biological matrix through a boundary surface is being detected by a light detector in order to determine a measurable physical light property which is changed by interaction with the biological matrix and which correlates with the glucose concentration of said matrix. The glucose concentration is ascertained in an evaluation step on the basis of said change of the physical light property determined in at least one detection step in comparison with a calibration. In order to achieve by such a method good analytical accuracy in reagent-free and non-invasive manner, for instance to observe the change of the concentration of the analyzed substance (monitoring) over an adequate time interval, a measurable parameter corresponding to the light transit-time within the biological matrix between a defined irradiation site and a defined detection site and correlating with the glucose concentration is determined in the detection step.

50 Claims, 9 Drawing Sheets

OTHER PUBLICATIONS

International Publication No. WO92/15988 published Sep. 17, 1992.

International Publication No. WO92/15861 published Sep. 17, 1992.

International Publication No. WO93/00856 published Jan. 21, 1993.

International Publication No. WO89/01758 published Mar. 29, 1989.

International Publication No. WO91/17697 published Nov. 28, 1991.

International Publication No. WO93/11701 published Jun. 24, 1993.

McCormick et al., SPIE, "Noninvasive measurement of regional . . . ", vol. 1431, 1991, pp. 294–302.

Coté et al., IEEE Transactions on Biomedical Engineering, "Noninvasive Optical Polarimetric Glucose . . . ", vol. 39, No. 7, 1992, pp. 752–756.

Liu et al., Analytical Biochemistry, "Characterization of Absorption and Scattering . . . ", 213, 1993, pp. 378–385.

Chira et al., Biomed. Technik, "Light Scattering by Blood Components . . . ", vol. 35, 1990, pp. 102–106.

Lakowicz, Analytica Chimica Acta, "Optical sensing of glucose using . . . ", 271, 1993, pp. 155–164.

Kruse–Jarres, J. Clin. Chem. Clin. Biochem., "Physico-chemical Determinations of Glucose in Vivo", vol. 26, 1988, pp. 201–208.

Laczko et al., American Institute of Physics, "2–GHz frequency–domain fluorometer", 57 (10) Oct. 1986.

Lakowicz et al, Anal. Chim. Acta, "Optical Sensing of Glucose using . . . " 271, (1993) pp. 155–164.

Duncan et al., University College London, "A Multiwavelength, wideband, intensity modulated optical spectrometer . . . ".

METHOD AND APPARATUS FOR THE ANALYSIS OF GLUCOSE IN A BIOLOGICAL MATRIX

TECHNICAL FIELD

The invention concerns a method and a device for analyzing glucose in a biological matrix.

BACKGROUND OF THE INVENTION

The expression "biological matrix" denotes a body fluid or a tissue of a living organism. Biological matrices within the scope of the invention are optically heterogeneous, that is, they contain a large number of scattering centers scattering the irradiated light. In the case of biological tissue, especially skin tissue, the scattering centers are formed inter alia by cell walls and other optically heterogeneous components contained in the tissue.

Body fluids and in particular blood also are optically heterogeneous matrices because they contain particles at which the primary radiation is scattered in a multiple manner. Milk and other liquids tested in foodstuff chemistry contain a high concentration of scattering centers, for instance in the form of emulsified fat droplets.

Generally in the qualitative and quantitative analytical determination of components of such biological matrices reagents or systems of reagents are used which react with the particular component to generate a physically detectable change in the reaction solution such as a change in its color, that can be measured as a measurement quantity. Using standard samples of known concentrations for calibration, a correlation is ascertained between the values of the measurement quantities for different concentrations and the particular concentration.

While such procedures allow highly accurate and sensitive analyses, on the other hand they require that a liquid sample, especially a blood sample, is removed from the body for analysis ("invasive analysis"). Such sample-taking is unpleasant and painful, and entails some risk of infection.

This is especially the case when an illness requires frequent analysis. The most significant example is diabetes mellitus. To avoid serious secondary diseases and critical patient Condition, this illness requires frequent, even continuous monitoring of the blood glucose content.

Accordingly, a number of procedures and devices already have been suggested to determine, in-vivo, the amount of glucose in the blood, tissue or other biological matrices in a non-invasive manner.

A survey of physical-chemistry (reagent-free) in-vivo determinations of glucose is provided by J. D. Kruse-Jarres "Physicochemical determinations of glucose in vivo", J. Clin. Chem. Clin. Biochem. 26 (1988), pp 201-208. Illustratively Nuclear Magnetic Resonance (NMR), Electron Spin Resonance (ESR) and infrared spectroscopy are cited as non-invasive procedures. However, none of these procedures have yet become practical. One reason is that exceedingly large and costly apparatus is required, which are wholly unsuited for routine analysis or for patient self-checking (home monitoring).

The present invention refers to a sub-set of such procedures wherein primary light is irradiated from a light source through a boundary surface bounding the biological matrix into this matrix and where light issuing through a boundary surface bounding said matrix is detected by a light sensor to ascertain a physical light property which is a function of its interaction with the biological matrix (without using reagents). The physical light property correlates with the glucose concentration in the biological matrix. Hereafter such a method step will be denoted as "detection step".

The physical light property correlated to the glucose concentration and determined (detected) in a detection step and which also may be denoted as "quantifiable parameter" will hereafter merely be called the "measurement quantity", for the sake of simplicity. However, this concept must not be construed as being limited to cases where the magnitude of the measurement quantity is measured in a common dimensional unit.

Because the methods discussed herein do not provide absolute measurements of glucose concentration, calibration will always be required (as in the conventional analytical procedures based on chemical reactions). For calibration generally the glucose concentration in a biological matrix with known glucose concentration is measured in at least one calibration step which is carried out in the same manner as the detection step. The particular glucose concentration of the biological matrix may be ascertained using any known or conventional procedure.

The glucose concentration is calculated in an evaluation step of the analysis from the change of the measurement quantity measured in at least one detection step when compared with at least one calibration step. The evaluation step comprises an evaluation algorithm whereby the glucose concentration is determined in a predetermined manner from the results of at least one detection step and at least one calibration step.

As a general rule the wavelengths of the light applicable to such methods are between approximately 300 nm and several thousand nm, that is, in the spectral range between near UV and infrared light. The expression "light" must not be construed as being restricted to the visible light spectrum.

Nearly all known procedures of this kind are based on spectroscopy. Spectroscopy is based on the interaction of irradiated primary light with the vibrational and rotational states of the molecules to be analyzed. The measurement quantity is the light intensity I which drops as a function of the optical absorption in the biological matrix and of the wavelength L. Typically the light attenuation is expressed as the extinction $E(L)=\log_{10}[I(L)/I_0(L)]$, with I being the intensity of the secondary light and $I_0$ the intensity of the primary light. To be able to detect spectral changes with sufficient accuracy, a sufficiently wide spectral range must be recorded with good wavelength-resolution during the detection step. In general the extinction is measured using at least two wavelengths at least about 50 nm apart and with a light bandwidth of less than 5 nm.

The vibrational and rotational ground states of glucose are in the IR range beyond 2,500 nm. Because of the strong absorption of the large amount of water always present in the biological matrices, these ground states cannot be used to analyze glucose in a non-invasive manner. In the range of the near infrared (NIR), the water absorption is reduced (this is the so-called "water transmission window"). The spectral analysis of glucose in this range is based on absorption by overtones and combined vibrations/oscillations of vibrational and rotational ground states of the glucose molecule (see above article by Kruse-Jarres and European patent document A 0,426,358).

Exceedingly severe difficulties are encountered when practically embodying a non-invasive glucose sensor which is based on the above principles, primarily because the measured signal (the change in absorption spectrum as a function of a change in glucose concentration) is very small, and this signal has to be detected in a strong background of interferences especially from the spectral absorption of water and other strongly absorbing components, among which is the red blood pigment hemoglobin.

Considerable and very diverse research has already been carried out to solve this problem. In many cases, the interferences are sought to be eliminated by suitably selecting the test wavelengths in combination with differential measurements. In particular the "two-wavelength spectroscopy" procedure is widely used, whereby a first test wavelength is selected in such manner that the glucose shall be as highly absorbing as possible at that wavelength, whereas a second wavelength is selected as a reference wavelength in such a way that the light absorption shall be substantially independent of the glucose concentration. Such and similar procedures are the objects for instance of the European patent document A 0,160,768; WO 93/00856 and U.S. Pat. No. 5,028,787.

In spite of all these endeavors, a practically operational non-invasive glucose sensor has not yet been provided.

A more realistic approach of using an in-vivo sensor which is based on spectral analysis refers to the analysis of substances having an optical absorption which is by several orders of magnitude higher than that of glucose. The most important example is the determination of hemoglobin (Hb) or its oxidized form $HbO_2$. These parameters providing information on the state of oxygenation of the blood, such sensors also are called oximeters. Prior publications describe numerous and different designs and procedures for noninvasive oximeters, operation with two-wavelength spectroscopy being prevalent. Reference is illustratively made to the patent documents WO 89/01758; EP A 0,286,142; EP A 0,353,619; WO 91/17697 and U.S. Pat. No. 5,057,695.

The European patent document 0,074,428 describes a method and a device for the quantitative determination of glucose by means of laser-light scattering. It is assumed therein that the glucose molecules scatter a light beam transmitted through the solution and that thereby the glucose concentration can be found. According to this theory, the solid-angle distribution of transmitted light intensity issuing from a test cell or a body part under examination is used as the measurement quantity for the glucose concentration. In particular the intensity of the transmitted light is measured in a solid-angle range where the change as a function of the glucose concentration is as large as possible and is compared with the intensity of the central beam passing straight through the sample.

An object of the invention is to provide a method for the analytical determination of glucose in a biological matrix and operating with simple means in a reagent-free and noninvasive manner, while allowing good analytical accuracy to observe, for instance, the change in the concentration of the analyzed substance (monitoring) over an adequate time interval.

This problem is solved by a method comprising at least one detection step and one evaluation step in the sense of the above discussions, wherein the measurable property correlating with the glucose concentration (that is a measurement quantity in the sense discussed above) is a parameter corresponding to the light transit-time inside the biological matrix between a defined site of irradiation and a defined site of detection. A corresponding device is also part of the solution of the problem according to the invention.

An important basis of the invention is the finding that the mean optical path length of photons inside an optically heterogeneous biological matrix is affected to a surprisingly high degree by the glucose concentration therein. Within the scope of the present invention, it was found that this dependence is large enough to determine the glucose concentration in vivo without reagents and at acceptable cost. This surprising effect can be explained as follows in the light of the present knowledge of the inventors.

The change in the glucose concentration causes a change in the index of refraction of the liquid contained in the biological matrix in which the glucose is dissolved. In turn the change in the index of refraction causes a change of light scattering by the scattering centers contained in the matrix. Each individual scattering depends only minutely on the glucose concentration because the change in the index of refraction is only approximately 0.002% per mmole. It was, however, discovered within the scope of the present invention that this extremely small effect can be used practically for glucose analysis provided that a parameter is detected which is characteristic of the transit time of photons which are multiply scattered in the biological matrix. In other words, the mean optical path length of photons (where said path length is the product of the transit time and the speed of light in the matrix) depends so much on the glucose concentration that a parameter (hereafter "transit-time parameter") corresponding to the photon travel-time can be used as a measure of the glucose concentration in the biological matrix.

The transit-time parameter in the above sense shall be any quantifiable light parameter which correlates with the transit-time and depends under the particular conditions predominantly on the light transit-time between the site of irradiation and the site of detection. Similarly to heretofore conventional measurement quantities correlating with the glucose concentration, the "determination" of a transit-time parameter does not require the measurement of absolute values in conventional units. It suffices that the result of the detection step is an electrical signal which unambiguously and reproducibly correlates with the transit-time and which can be related (in the evaluation step) to a value of the same transit-time parameter which was determined (in a calibration step) in the same manner in a biological matrix having a known glucose concentration.

In a first embodiment of the invention, the transit time is ascertained directly by radiating a short pulse of primary light into the biological matrix at each detection measurement and by detecting the pulse issuing from the detection site. For such measurement considerable equipment is required since the transit time between the site of irradiation and the site of detection is exceedingly short, of the order of $10^{-9}$ seconds.

Therefore, a test method is preferred wherein the primary light is modulated with a carrier frequency, whereby waves of light intensity propagate in the biological matrix, the wavelength corresponding to the quotient of the speed of light in the biological matrix and the frequency of modulation. The phase shift of the secondary light is used as the transit-time parameter. The transit time dt in a nonabsorbing material depends directly linearly on the phase shift $d\phi$, i.e. $dt = d\phi/\Omega$, with $\Omega$ the frequency of modulation of the primary light. Under the practical conditions of the present invention, absorption attenuation is comparatively low and such conditions apply in good approximation.

To assure the required analytical accuracy, a measurement technique is needed which allows determining minute phase shifts at high frequencies with good sensitivity and reproducibility. Such techniques are known, and are used, illustratively, in the chemical analysis art to determine the fluorescence life time of fluorescent dye molecules and for time-resolved spectroscopy.

Determining the life time of fluorescent species is conventionally used in analytical procedures in which a fluorescent label is, by means of a specific binding reaction, provided on the substance being analyzed. The fluorescence life time is determined as the measurement quantity in a part of such procedures ("phase fluorometry"). To be able to determine the very short lives, which as a rule are less than 100 ps, RF (radio-frequency) modulated spectrometers have been developed, which operate by modulating the light at a frequency between about 100 MHz and several GHz. A significant example is the heterodyne procedure, wherein the signal received by the detector is mixed with a second periodic signal of a frequency deviating by a few kHz from the former signal. The resulting differential signal is processed and measured using a lock-in amplifier or another narrow-band selective amplification procedure. A high-performance apparatus for such measurements is described by J. R. Lakowicz et al., "2-GHz frequency-domain fluorometer", Rev. Sci. Instrum., 57, 1986, pp 2499–2506. A method for analyzing glucose using phase-modulation fluorimetry is known from J. R. Lakowicz and B. Maliwal, "Optical sensing of glucose using phase-modulation fluorometry", Analytica Chimica Acta, 271, 1993, pp 155–164. This is an in-vitro test, with sampling performed in conventional, invasive manner, employing the required fluorescent-labeled reagents which must be mixed with the sample.

Time-resolved spectroscopy was developed by B. Chance for in-vivo analysis and is recommended by him primarily as a further development of two-wavelength spectroscopy (U.S. Pat. Nos. 4,972,331; 5,119,815; 5,122,974; 5,167,230 and 5,187,672). The examples shown therein relate to strongly absorbing substances, in particular pigments and the above mentioned oxygenation parameters Hb and $HbO_2$.

These documents are concerned with a basic problem of the spectroscopy of scattering media, for instance biological tissues, namely lack of knowledge of the optical path length. This knowledge is required to quantify the measured absorption spectra and to compute the concentration of an absorbing substance. In a non-scattering medium the optical path length is the length of the optical cell. In a scattering medium on the other hand, there is a statistical distribution of path lengths due to the large number of scattering processes. Using time-resolved spectroscopy and RF-modulated spectroscopy, it is possible to measure the randomly distributed, mean optical path length in the scattering medium or to associate it with the particular absorption value.

A. Duncan et al., in their publication entitled "A multi-wavelength, wide-band, intensity-modulated optical spectrometer for near-infrared spectroscopy and imaging", Proc. SPIE 1888, 1993, pp 248–257, describe a more recent development in this field.

SUMMARY OF THE INVENTION

The techniques described in the above publications to determine the transit times or phase shifts are also suitable for the present invention. As regards the measurement techniques, therefore, reference is made to the known and published procedures. However the invention differs foremost and basically from time-resolved spectroscopy because the invention is not based on the wavelength-dependent optical absorption of the analyzed substance, i.e., the invention is not a spectroscopic procedure. As elucidated below, absorption by the glucose itself is so minute even in the spectroscopically optimal range of wavelengths that it does not sensibly affect the light transit-time in a biological matrix. Moreover and preferably the tests according to the invention are carried out outside the range of wavelengths which would appear spectroscopically optimal. The invention does not require the measurement at (at least) two sharply defined wavelengths within a broad spectrum as is necessary in a spectroscopic procedure. Rather one measurement at one wavelength is sufficient, without the need for cumbersome narrow-band selection (for instance filtering) of the primary or secondary light.

Compared with the previously known procedures of non-invasive, reagent-free glucose determination, in particular spectroscopic determinations in biological matrices, the invention foremost offers the following advantages:

—The determination of the transit-time parameter is substantially independent of the absolute light intensity of the detected secondary light; therefore fluctuations in the optical coupling between the light emitter and light sensor at the matrix boundary surface are practically without effect.

—The accuracy of measurement is affected less by changes in optical absorption of highly absorbing interfering substances, in particular hemoglobin and water; such interference is critical in spectroscopic methods; illustratively even relatively slight fluctuations in the volume of blood of the tissue being tested cause such strong fluctuations in the measured secondary light intensity that such a noise signal exceeds the useful signal by several orders of magnitude; while the transit-time parameters are not fully independent of absorption changes in the matrix, the interference effect is less; moreover the wavelength of the primary light can be placed within a spectral range wherein the absorption of interfering substances is comparatively small and above all is constant.

—The dependence of the transit time on the glucose concentration is so large that even at comparatively short measurement distances of less than 4 cm, (preferably 3 cm at most, even more preferred, at most 2 cm), between the irradiation site and the detection site in a skin tissue, adequate accuracy of measurement can be achieved; this is highly significant because on one hand the intensity of the secondary light becomes so low at larger distances that it can no longer be detected with economical test equipment and because on the other hand as regards the skin, the glucose concentration preferably is measured tightly underneath the skin surface; the larger the measurement distance, the more the testing refers to lower tissue layers.

BRIEF DESCRIPTION OF THE DRAWINGS

The invention is elucidated below by means of embodiments shown in the Figures.

DESCRIPTION OF THE PREFERRED EMBODIMENTS

Figure 1:
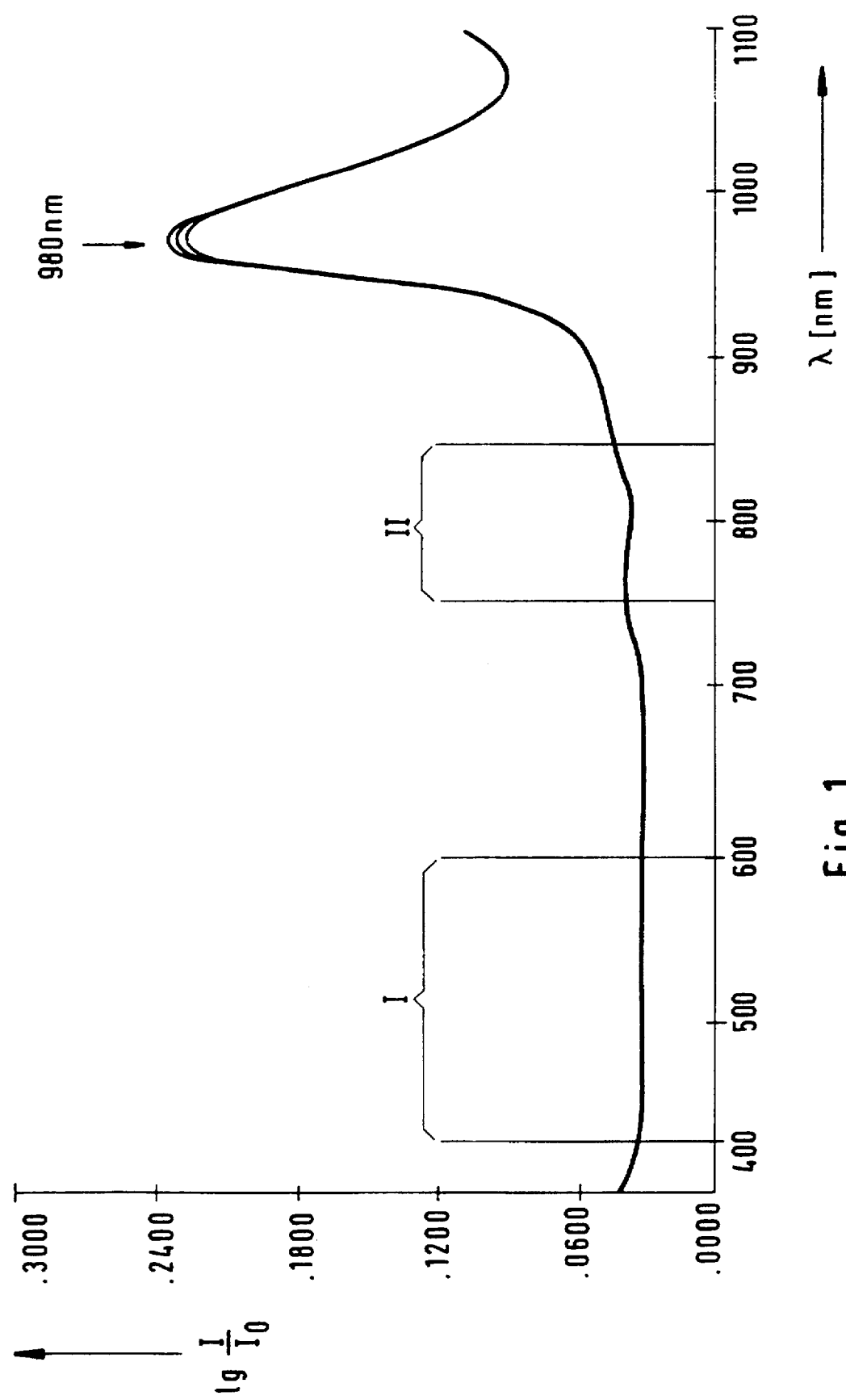
FIG. 1 is an absorption spectrum of glucose in water, for different glucose concentrations, within a first range of wavelengths.

FIG. 1 shows an absorption spectrum of glucose in water. The base-10 log of the ratio of measured to irradiated intensity ($Log_{10} I/I_0$) when transmitted through a cell thickness of 1 cm is plotted for four glucose concentrations, namely 0, 1, 5 and 10%. It becomes apparent that these spectra of four concentrations differ only slightly in a narrow range of wavelengths at about 980 nm. The maximum signal difference between the measurement quantity for pure water and for the 10% glucose solution is less than 2% at that wavelength. The difference is even less at other wavelengths. Furthermore the variation in glucose concentration used in the experiment is much higher than for the real physiological glucose concentration. With respect to a change of glucose of 100 mg/dl which is realistic in the physiological range, the change at 980 nm is less than 0.02%. The rate $dI/dC$ of the measurement signal I as a function of the glucose concentration C is denoted hereafter as the "relative signal change" and is expressed quantitatively in % for each 100 mg/dl change of glucose concentration.

Figure 2:
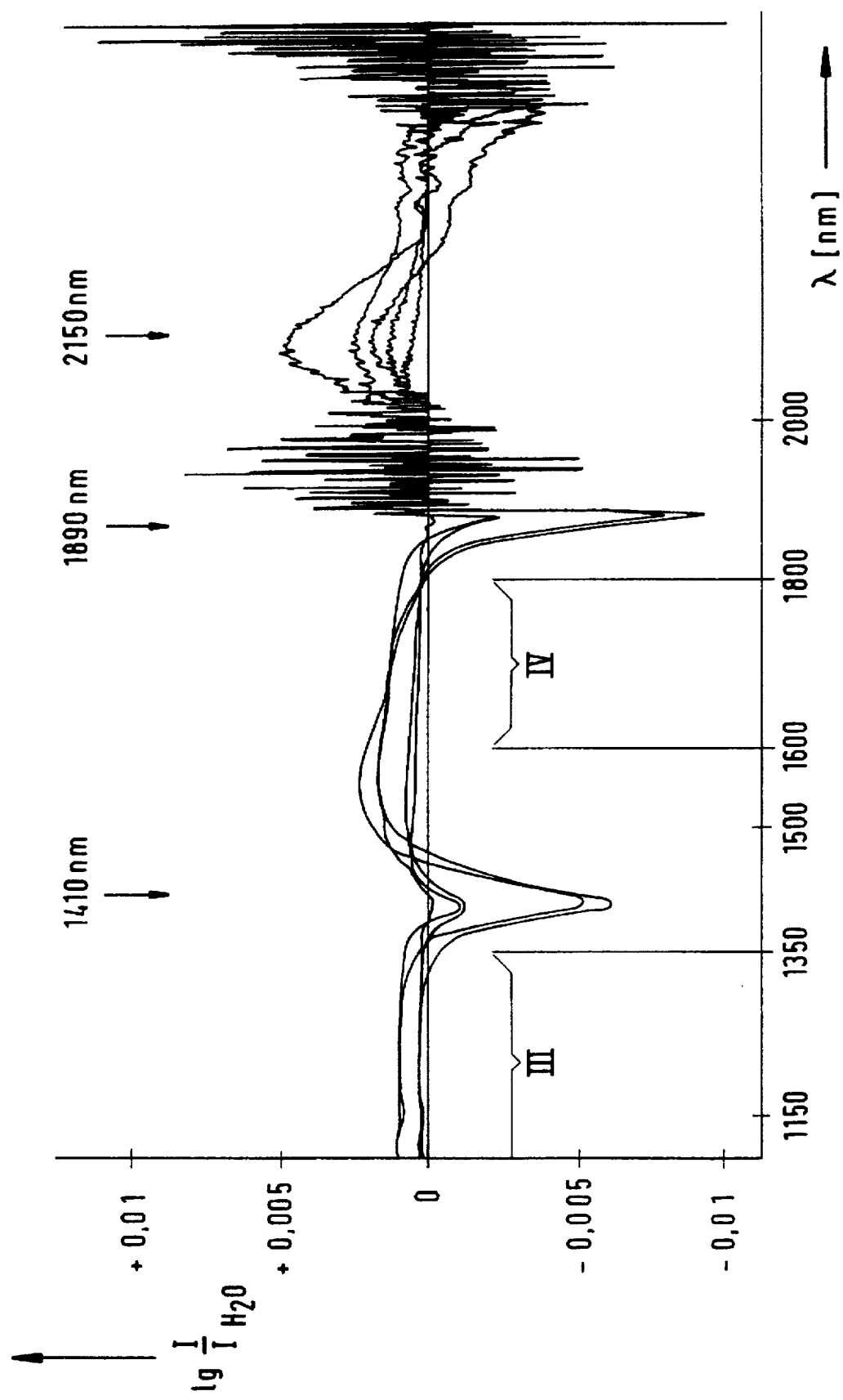
FIG. 2 is a differential absorption spectrum of glucose in water, relative to pure water, in a second range of wavelengths, for different glucose concentrations.

FIG. 2 shows a similar spectrum in the adjoining spectral range from about 1,100 nm to 2,500 nm. This is a differential spectrum for glucose concentrations between 0 and 600 mg/dl relative to pure water. Negative values indicate absorptions less than that of pure water. The maximum total effective change in signal intensity is less than 0.3%, that is a mean signal change of less than 0.05% per 100 mg/dl change in glucose concentration.

FIGS. 1 and 2 show that the dependence of the optical absorption on the glucose concentration is extremely small in a wide spectral range. Spectral ranges wherein the relative signal change $dI/dC$ in a transmission measurement of a clear glucose solution is less than 0.01% per 100 mg/dl change in glucose concentration are designated as spectral ranges with "little" dependency of absorption on glucose concentration. Based on the measurement results shown in FIGS. 1 and 2, the wavelengths at about 980 nm; 1,410 nm; 1,890 nm and 2,150 nm should be considered as best suited for the spectroscopic glucose analysis.

It may be shown from the test results shown in FIGS. 1 and 2 that even at the "spectroscopically optimal" wavelengths, the absorption of an aqueous glucose solution depends only so little on the glucose concentration that any changes in the light transit-time caused by such changes in absorption would fall short by several orders of magnitude to allow practical measurement. This fact shows that the correlation between the light transit-time in a biological matrix and the glucose concentration which was found within the scope of the invention cannot at all be explained by optical absorption caused by glucose.

Within the scope of the present invention, the ranges of wavelengths with little absorption of an aqueous glucose solution denoted by Roman numerals in FIGS. 1 and 2 are especially preferred, namely I. 400 to 600 nm, II. 750 to 850 nm, preferably 780 to 825 nm, especially-preferred 800 to 805 nm, III. 1,050 to 1,350 nm, preferably 1,200 to 1,300 nm, and IV. 1,600 to 1,800 nm, preferably 1,630 to 1,770 nm, especially-preferred 1,630 to 1,670 nm or 1,730 to 1,770 nm.

Preferably, the primary light shall be approximately monochromatic. In practical terms, "monochromatic" shall denote that the major part of the intensity shall be emitted with a pronounced maximum within a defined range of wavelengths, or the detection is limited to a correspondingly defined range of wavelengths. The half-width should be less than 100 nm, and preferably less than 50 nm. Contrary to the case of the spectroscopic procedures for non-invasive glucose analysis, comparatively wide-band light sources with half-widths larger than 20 nm such as light emitting diodes (LED's) or other semiconducting light sources can be used without requiring subsequent spectral selection. As a result, equipment economy is significantly enhanced. Where "wavelength" of the light source or primary light is referred to, it means the wavelength of the intensity maximum.

Contrary to the case of known spectroscopic procedures, it suffices in the invention that the detection step is carried out at only one particular wavelength. Because the measurement signal is largely independent of wavelength, those ranges of wavelengths may be selected for the measurement in which interference by strongly absorbing substances is minimized. In the range around 802 nm, the measured intensity is approximately independent of the concentration ratio of Hb to $HbO_2$ because these substances have an isosbestic point there. This applies also within a wide isosbestic range between 1,200 and 1,300 nm. In addition, the absorptions of hemoglobin and water are about equally large in this range. As a result, especially good independence of the measured intensity from the relative ratio of Hb, $HbO_2$ and $H_2O$ is achieved.

When empirically checking the method of the invention, it was found that comparatively short wavelengths, in particular between 400 and 600 nm, are likely to be especially advantageous because of their relatively shallow depth of penetration into biological tissue. Empirical observation shows that this is advantageous especially because of the more uniform distribution of the blood in the upper skin layers and possibly also because of improved correlation of the detected glucose concentration with blood glucose.

Figures 3, 4:
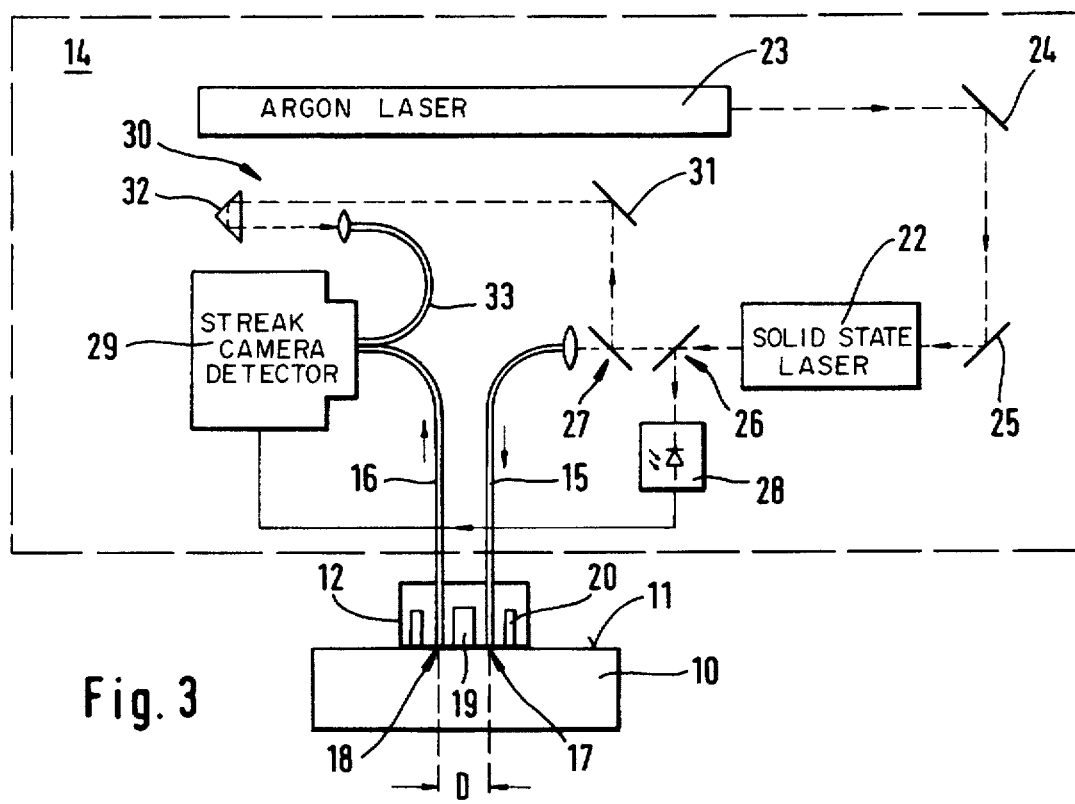
FIG. 3 is a functional diagram of a first embodiment of the invention wherein the light transit-time is determined directly.
FIG. 4 is a plot of a secondary-light pulse measured by means of the equipment of FIG. 3.

FIG. 3 is a diagram of the experimental set-up for measuring the transit time of a biological matrix 10 shown only symbolically as a rectangle. A measuring head 12 is in contact with a boundary surface 11 of the biological matrix 10. Preferably the biological matrix 10 is skin tissue, especially at the finger pad, at the abdominal wall, at the nail bed, at the lip, the tongue or the human inner upper arm, in which case the boundary surface 11 is formed by the skin surface. An analysis according to the invention can also be advantageously carried out at the sclera tissue.

Fiber-optics cables 15 and 16 run from transit-time measuring equipment denoted overall by 14 to the measuring head 12. The first fiber-optics cable 15 denoted as the transmitter cable radiates light into the biological matrix at an irradiation site 17. The other fiber-optics cable 16 serves for detection of light emerging from a detection site 18 and accordingly is denoted the detection cable.

Moreover the measuring head 12 includes means for measuring the temperature of the biological matrix 10 in the test area between the irradiation site 17 and the detection site 18 and, in a further preferred embodiment mode, to keep the temperature constant. For that purpose FIG. 3 symbolically shows a central IR temperature sensor 19 and an annular resistance heater 20. The heating output from the heater 20 is regulated by means of a control device (not shown) in such a way that the test-area temperature is kept constant.

The transit-time test equipment essentially consists of a light source in the form of a mode-coupled solid-state laser and of a streak-camera as the detector.

In the example shown, the solid-state laser 22 is a titanium-sapphire laser optically pumped by an argon laser 23 by means of two deflecting mirrors 24 and 25. Short light pulses with a pulse width of about 2 ps ($2 \times 10^{-12}$ s) and a repetition rate of 82 MHz are thus generated. The light wavelength was adjustable between 740 and 900 nm in the experimental set-up, that is, in the near infrared. The mean power output of the solid-state laser used was about 1 W.

The light from the solid-state laser 22 passes through two beam splitters 26, 27 and is coupled into the transmitter fiber-optics cable 15. Part of the light passes through the first beam splitter 26 and is directed at a photodiode 28 the output signal of which serves to synchronize the streak-camera 29 used as detector.

A further partial beam is deflected by the second beam splitter 27 into a delay path 30 consisting in the example shown of a further deflection mirror 31, a 180° reflecting prism 32 and a fiber-optics cable 33 connected to the streak camera 29. Thereby both the light passing by means of the fiber-optics cables 15 and 16 through the biological matrix 10 and the light passing along the delay path 30 are measured in the same manner by the streak camera 29.

The time base of the transit-time measuring equipment 14 is adjusted before the actual analytical determination. For that purpose the ends of the fiber-optics cables 15, 16 are removed from the measuring head 12 and are moved tightly together. This condition represents the transit time t=0. In actual measurement the ends of the fiber-optics cables 15 and 16 are located at the irradiation and detection sites 17 and 18, respectively at a defined measurement distance D on the boundary surface 11 of the biological matrix 10. In this state the delay path 30 is increased until both the reference signal passing along the delay path 30 and the measurement signal transported by the cables 15, 16 are detected in the time display window of the streak camera. In this manner the transit time from the irradiation site 17 to the detection site 18 can be measured with an accuracy of a few ps.

FIG. 4 shows a typical test result. It represents the light intensity vs time measured at the detection site 18, which results from a pulse of the solid-state laser 22. It is clear that the short delta-pulse of the primary light is broadened substantially by the multiple scattering in the biological matrix 10 and the resulting multiplicity of different path lengths from the irradiation site 17 to the detection site 18. The half-width of the shown secondary-light pulse is about 1 ns.

The curve of the secondary-light pulse allows computing the mean transit time <t> of the light from the irradiation site 17 to the detection site 18, which corresponds to the mean optical path length between these two sites. This mean transit time is shown in FIG. 4. In this case it is approximately 1.2 ns.

Figure 5:
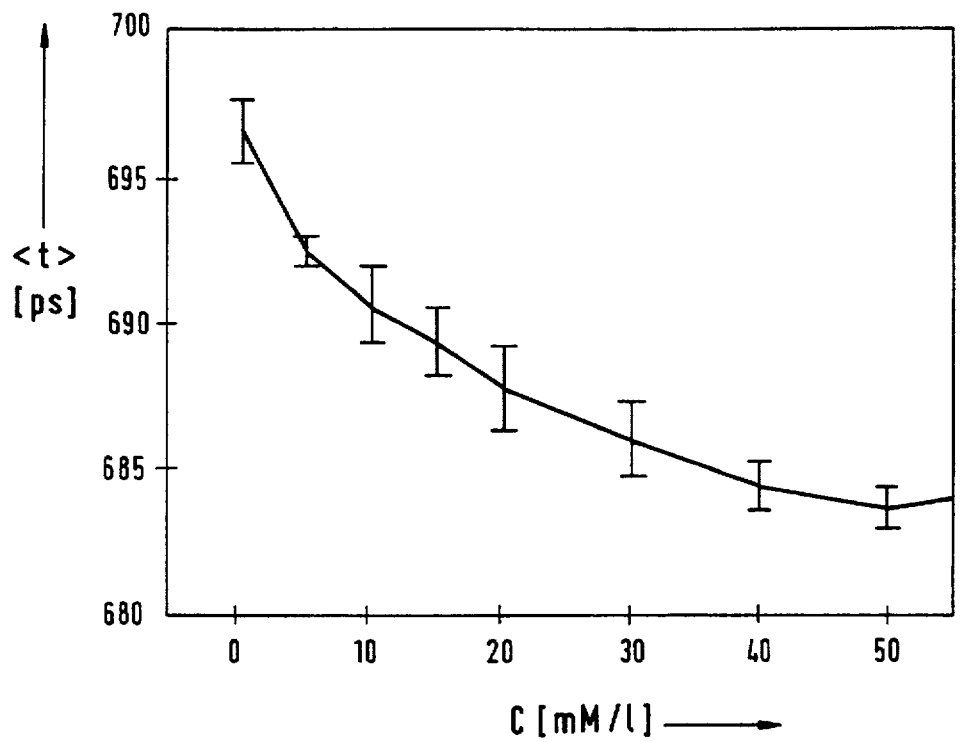
FIG. 5 is a plot of a correlation function between transit-time and glucose concentration measured by means of the equipment of FIG. 3.

FIG. 5 shows the dependence of the mean transit time <t> in ps on the glucose concentration in mmoles. An experimental model of a biological matrix was used consisting of a suspension of latex particles (approximately 2.5 μm in diameter) in water, to which an IR dye was added. The concentrations of particles and dye were selected in such manner that the absorption and scattering coefficients were approximately those of typical tissue values. The measurement distance D between the irradiation site 17 and the detection site 18 was about 15 mm.

FIG. 5 clearly shows that the mean transit time <t> drops as the glucose concentration rises. Even though this effect is relatively small, it can be determined with good accuracy. The invention offers a special advantage in this respect in that compared with glucose in-vivo determinations based on light intensity measurement, its measurement quantity, i.e. the transit time, is significantly less sensitive to optically reproducible coupling to and decoupling from the irradiation and detection sites respectively.

Figure 6:
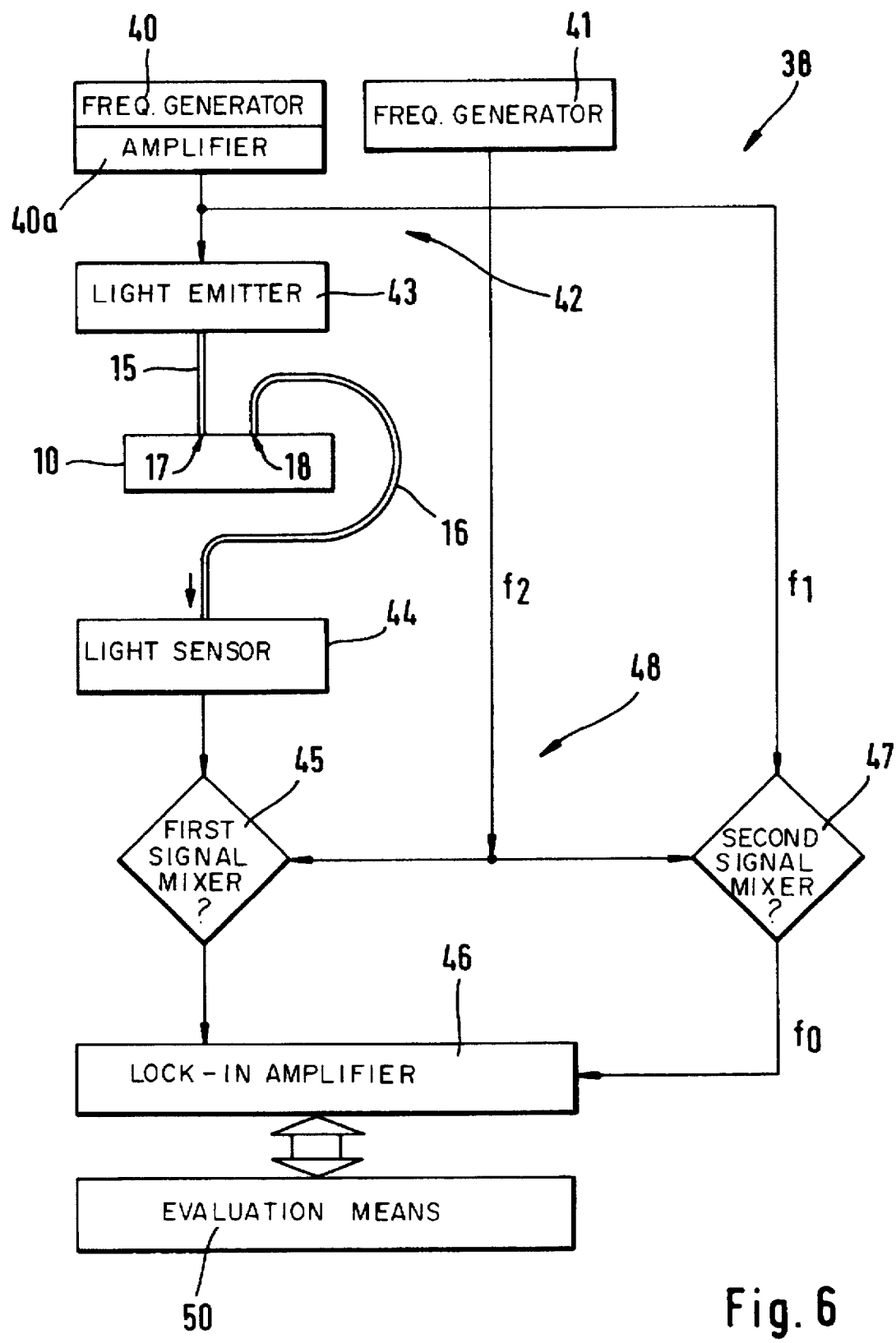
FIG. 6 is a block diagram elucidating a second embodiment of the invention to determine the light phase-shift.

FIG. 6 shows an illustrative block diagram of equipment for measuring the phase shift (phase measurement device). The measurement technique, namely heterodyning, is also used in phase fluorometry.

A frequency generator 40 generates a high-frequency, periodic oscillation which, passing through an amplifier circuit (driver stage) 40a drives a light emitter 43, for instance a LED. As a result, the primary light from the light emitter 43 is modulated with a high frequency $f_1$ denoted as the carrier frequency. The frequency should be more than 50 MHz, preferably more than 200 MHz, especially-preferred more than 500 MHz. The light from the emitter 43 passes through a first fiber-optics cable 15 to an irradiation site 17 to serve as the primary light just as in the embodiment of FIG. 3 and is irradiated into the biological matrix 10. The light irradiation means 42 composed of the components 40, 40a, 43 and 15 may also be implemented in some other manner. Various possibilities are known from the initially cited literature and many other publications.

The light emerging from the biological matrix 10 at a detection site 18 is detected by detection means 48 including in the shown embodiment a detection fiber-optics cable 16 to transmit the secondary light to a light sensor 44. The sensor 44 transforms the light intensity into a corresponding electric output signal which is fed to a signal mixer 45. The signal mixer 45 simultaneously receives the output signal from a second frequency generator 41 which is synchronized with the frequency generator 40. The output frequency $f_2$ of generator 41 differs only slightly (for instance by $f_0$=1 kHz) from the frequency $f_1$ of the first frequency generator 40. The differential frequency $f_0$ is selected in such manner that it synchronizes a lock-in amplifier without problems and that the intrinsic noise of the required preamplifiers is low.

The output of mixer 45 is fed to the input of a lock-in amplifier 46. The outputs from the frequency generators 40 and 41 are applied to a second mixer 47. The output of mixer 47 is the reference signal applied to the lock-in amplifier 46.

The lock-in amplifier 46 generates two output signals corresponding respectively to the real and imaginary components of the periodic measurement signal. The real and imaginary components allow computing the phase difference and the AC and DC amplitudes relative to the reference signal. The phase measurement device may also be implemented in another manner. Many variations of electronics for measuring such phase shifts are known and are applicable to the present invention. In this regard reference is made in particular to the above cited literature concerning phase fluorometry and time-resolved spectroscopy.

The phase shift of the secondary light measured at the detection site 18 relative to the primary light irradiated at the irradiation site 17 is a measure of the light transit-time in the biological matrix and hence a measure of glucose concentration. Evaluation means 50 are provided, appropriately in the form of a microcomputer for the evaluation step required to compute the glucose concentration (that is to carry out an evaluating algorithm).

Figure 7:
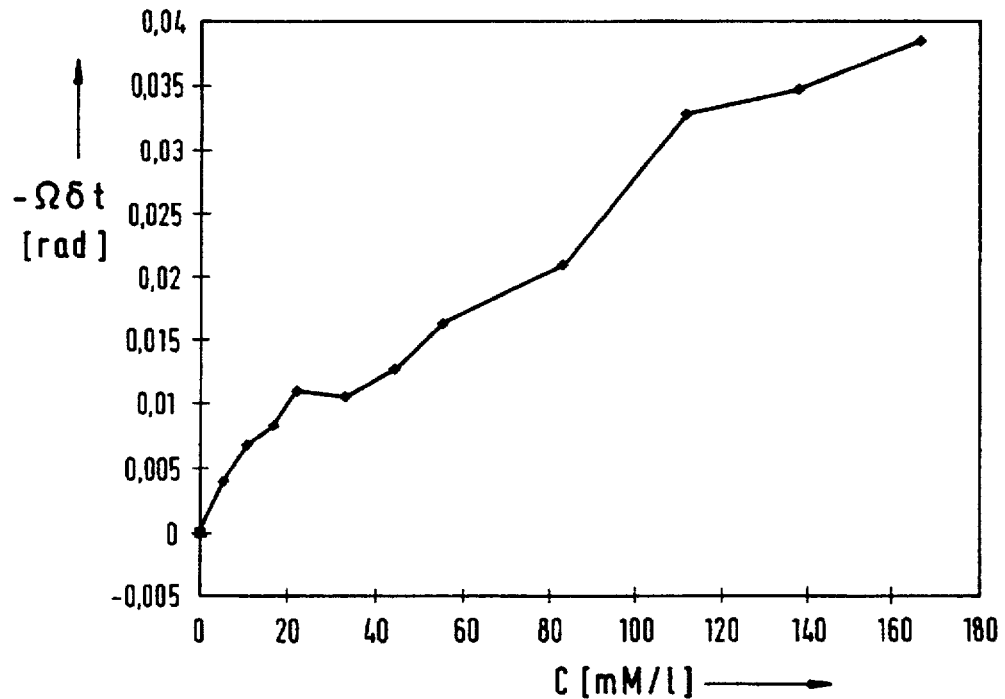
FIG. 7 is a plot of a correlation function between phase-shift and glucose concentration measured by means of the equipment of FIG. 6.

FIG. 7 shows test results obtained by an apparatus designed essentially according to FIG. 6. A suspension of fat droplets in water (intralipid) in a 25 mm thick cell was tested. Testing was performed in a transmission mode, the fiber optics for irradiating the primary light and for detecting the secondary light being mounted on opposite cell sides directly on the cell walls.

FIG. 7 shows the phase shift as a function of glucose concentration at a wavelength L=690 nm. The phase shift corresponds to the negative product of the angular frequency of the modulation $\Omega$ and the change in transit-time $\delta t$ and is accordingly denoted by $-\Omega\delta t$. The shown increase in this measurement quantity therefore corresponds to a decrease in transit time and thus is in conformity with the test results shown in FIG. 5.

Figure 8:
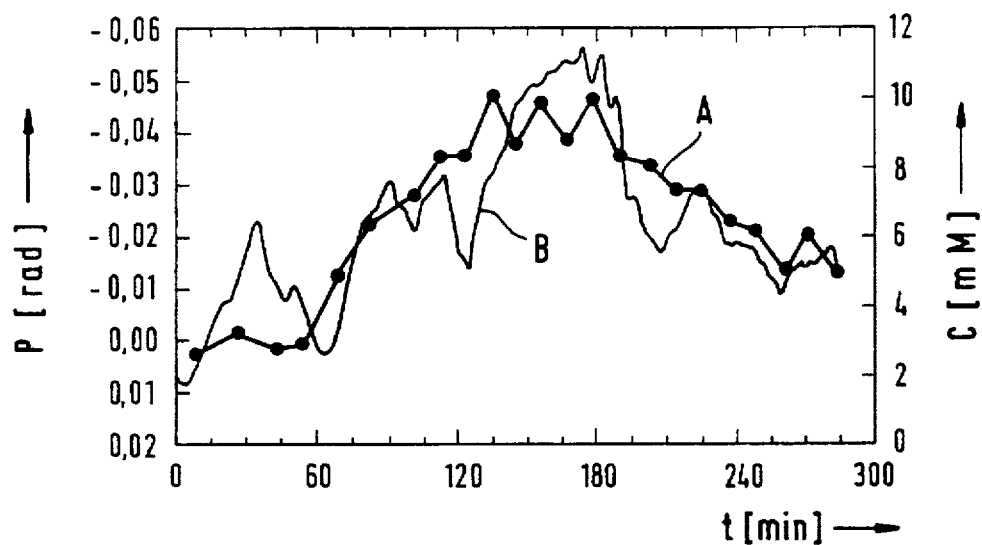
FIG. 8 is a plot comparing the results from tissue measurements obtained by the method according to the invention with results from a conventional procedure.

FIG. 8 shows the test results of glucose analysis in tissue using the method according to the present invention. It shows the glucose-concentration C (right ordinate, black dots, curve A), and the phase shift P (left ordinate, curve B), versus the time t in minutes. The measurement values of curve A were obtained conventionally in invasive manner by taking and by analyzing blood samples in a test-strip analyzer, whereas curve B was measured using the method according to the present invention. It becomes clearly apparent that the method according to the present invention correlates well with conventional measurements. The short-term fluctuations appearing in FIG. 8 can be reduced by time averaging.

Calibration is required in every embodiment of the invention to determine the absolute glucose concentration, identical detection steps being carried out on a biological matrix with known glucose concentration. From such calibration measurements a calibration curve of the functional relationship between glucose concentration and transit-time parameter is obtained in conventional manner. If the calibration curve is linear, generally two calibration detection-measurements for two different glucose concentrations are required. If the calibration curve is not straight, a larger number of calibration measurements are made.

As already mentioned, the measurement of the phase shift (as an "indirect transit-time parameter") offers the advantage over the direct determination of transit-time that adequate accuracy of measurement is achieved with substantially simpler test equipment.

Within the scope of the present invention, the AC amplitude of the secondary light is preferably determinded in addition to the phase shift and used in the evaluation step for the determination of the glucose concentration. The AC amplitude of the secondary light (in relation to the AC amplitude of the primary light) can easily be measured in combination with the phase shift. This was described in the context of FIG. 6 and also applies to other known measurement procedures.

Furthermore when carrying out such measurements the DC amplitude of the secondary light can be measured in relation to the DC amplitude of the primary light. In a further preferred embodiment of the invention, use is made of the measured DC component of the secondary light, in relation to the DC component of the primary light, for determination of the glucose concentration in the evaluation step, in addition to the phase shift.

If a plurality of measurement quantities such as phase shift and AC or phase shift and DC are used to determine a single glucose concentration an evaluation algorithm obviously has to be used which is suitable to correlate a plurality of input variables (phase shift, AC, DC) with one output variable (glucose concentration C).

In the simplest case such an algorithm may comprise a predetermined mathematical operation for deriving an intermediate value from the measured input variables. The intermediate value can be called a measurement result R. The measurement result R may then be linked with the glucose concentration C in the familiar manner by calibration with at least two, but preferably with several standard samples of known glucose concentration.

Mathematically more sophisticated numerical methods have recently been increasingly used in analytical technology for improving the correlation between the measured quantities (input variables) and the respective unknown concentration (output variables) and hence for improving the analytical accuracy. These include iterative methods for optimal description of the relation of input variables and output variables. Multi-linear and nonlinear algorithms can be used to take into consideration several factors required for the evaluation of analytical measurements. This is also possible in the present invention and can be used to relate the measurement values of phase shift, AC and DC to the concentration. Moreover such procedures also allow to take into account further influencing factors (for instance the temperature at the measurement site).

As already mentioned, in a preferred implementation a frequency in excess of 500 MHz is used, which is very high compared to conventional procedures. Such a feature can be advantageous within the scope of the present invention by thereby keeping the depth of penetration of the light path shallow between the sites of irradiation and detection, as a result of which the glucose concentration can be measured in controlled manner in the uppermost skin layers.

Where called for, accuracy may be improved by modulating the primary light with a plurality of different carrier frequencies while determining the transit-time parameter in the form of the phase shift.

The geometric requirements concerning the dimensions of the irradiation site 17 and the detection site 18, further the location of these sites on the boundary surface 11 of the biological matrix 10 and especially regarding the measurement distance D can be determined individually and empirically. The following fundamentals should be observed.

The expressions "site of irradiation" and "detection site" must be construed geometrically, namely as being those elements of the boundary surface of a biological matrix that are crossed by the light beams which determine the transit-time parameter in the particular detection step. Where hereafter distances between the sites of irradiation and detection are stated, they will refer to the center of the particular irradiation site or that of the detection site and are measured in the direction of the gap, i.e. of the shortest distance, between the irradiation site and the detection site.

In order to relate the transit-time with high resolution to the respective measurement distance, the size of the irradiation site and that of the detection site in the direction of the distance must not be too large. Preferably it shall be less than 2 mm, especially less than 1 mm.

In order to assure the multiple light scattering in the biological matrix required for the effect of the invention, the irradiation and detection sites must be so configured relative to one another that the light on its path from the irradiation site to the detection is scattered many times. This can be achieved by a sufficient length of the measurement distance. Typically the mean free path of photons in tissue or blood is between 0.01 and 0.1 mm. The path of the light within the biological matrix always is longer than the straight line between the irradiation and detection sites. Therefore a measurement distance of a few mm already makes sure that the condition of multiple scattering is met.

To achieve as large as possible a dependence of the measurement signal on the glucose concentration, the measurement distance between the irradiation and detection sites shall be as large as possible. However, beyond an upper limit to be determined in each particular case, the signal-to-noise ratio becomes too small due to the decreasing intensity of the secondary light. Generally therefore the measurement distance shall be less than 4 cm, preferably less than 3, and especially-preferred less than 2 cm. These measurement distances are clearly less than those which are discussed within the scope of time-resolved spectroscopy. This again shows the strong effect of the present invention compared with known methods. Even though in time-resolved spectroscopy of the oximetry-parameters the light absorption of the analyzed substance is higher by several orders of magnitude, large measurement distances are considered essential therein to achieve adequately large dependence of the phase shift on the concentration of the analyzed substance. In the glucose determination of the present invention the measurement signal is larger in spite of the fact that the optical absorption of glucose is smaller by several orders of magnitude. This provides additional proof that the present invention is based on a wholly different mechanism of interaction between light and the biological matrix.

For optimizing the accuracy of measurement it may be especially advantageous to determine the transit-time parameter correlating with the glucose concentration for several different measurement distances between the irradiation and detection sites. By this manner the ascertained functional dependence of the light transit-time (with the same light wavelength) on the measurement distance between the irradiation and detection sites may be advantageously used in the evaluation step to determine the glucose concentration.

If this functional dependence on the measurement distance is measured for other measurement quantities in addition to phase shift such as the AC- and/or DC-amplitudes (of the secondary light compared to the primary light) a substantial number of measurement data may be used for correlating with the glucose concentration. In such cases in particular the numerical mathematical methods mentioned before are suitably used in the evaluation step. Especially a multivariate regression algorithm such as PLS or a learning (computer-)system (neural network) may be used.

Figure 9:
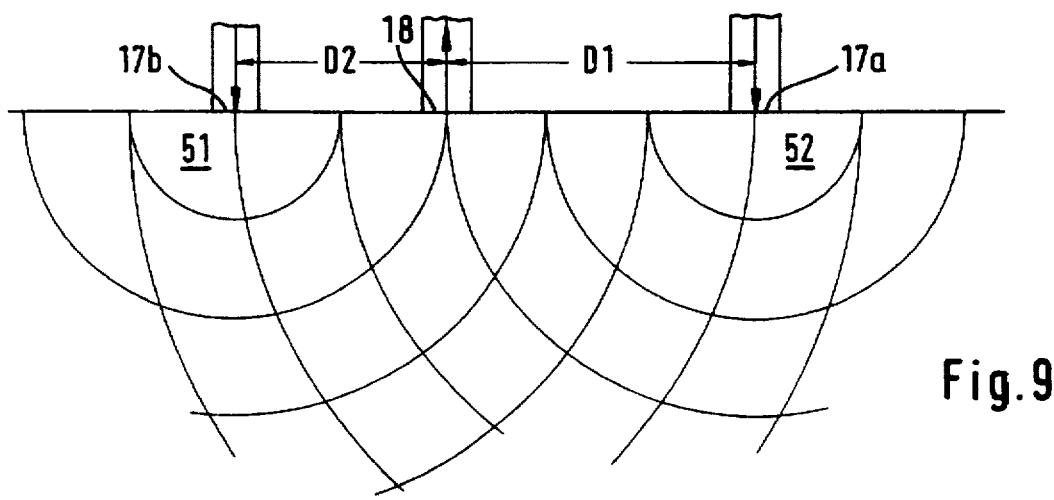
FIG. 9 is a functional diagram showing the configuration of irradiation and detection sites for a specific embodiment of the invention to determine the phase shift serving as the transit-time parameter.

FIG. 9 illustrates another preferred embodiment wherein the primary light is simultaneously irradiated at two different irradiation sites 17a, 17b. The light intensity waves 51, 52 shown symbolically in the Figure and propagating in the biological matrix are superposed. When appropriately selecting the test conditions—which are discussed in more detail below—such a configuration allows ascertaining the change in a measurement quantity of the detected light at a detection site 18 located between the irradiation sites 17a and 17b, where said ascertained change is especially sensitive to the difference in light transit-times between the two irradiation sites 17a, 17b and the detection site 18 between them.

Figure 10:
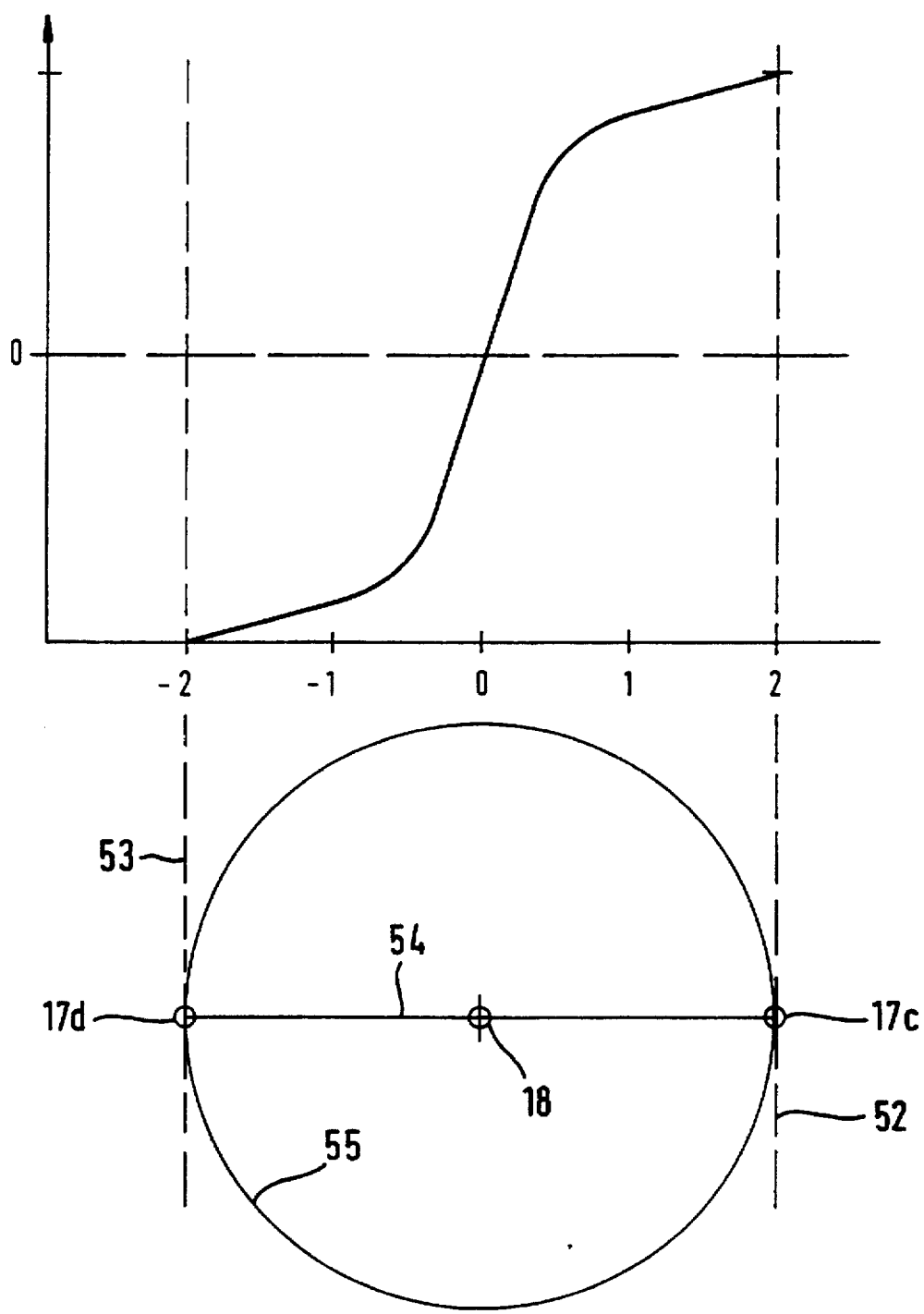
FIG. 10 is a schematic topview of a biological matrix to elucidate the positioning of two irradiation sites and one detection site in a further and preferred embodiment of the invention in conjunction with a plot illustrating the effect achieved thereby.

FIG. 10 explains the effect based on the preferred configuration of FIG. 9. First it must be borne in mind that a superposition of light intensity waves rather than interference is taking place. The wavelength of the intensity waves corresponds to the quotient of phase velocity of the wave in the medium to the modulation frequency and can be estimated to about 0.1 m.

To achieve the desired high sensitivity of detection, the intensity, modulation level and phase of the primary light irradiated at the irradiation sites 17a and 17b are so mutually matched as to produce, in the vicinity of the detection site, a minimal AC amplitude and maximum dependence of the measured signal as a function of change in detection site. The top portion of FIG. 10 shows a plot of the AC signal resulting from superposition when two irradiation sites are present at equal measurement distances D=+2 cm and −2 cm from a midway detection site 18. Such a configuration is shown in the lower half of FIG. 10.

When the distances are equal and the light sources emit equal intensities, the aforementioned condition will be met when the primary light at the irradiation sites 17c and 17d is modulated approximately in out-of-phase manner, that is with 180° phase-shift.

If, for such a configuration, the mean light path between one of the irradiation sites and the detection site changes more markedly than between the other irradiation site and the detection site, then the area where the phase jump is observed is also shifted. This shift is much more sensitively determined than for a configuration with a single irradiation site, provided that the detection site is located in the steep region of the curve of FIG. 10.

This effect can be used to sense the glucose concentration when changes in glucose concentration affect the light path more markedly on one side of the configuration than on the other. This condition can be met by making the measurement distance D1 between the first irradiation site and the detection site different from the measurement distance D2 between the second irradiation site and the detection site, as shown in FIG. 9. Alternatively, when testing a tissue, the location of the measuring head on the tissue surface (and hence the location of the irradiation and detection sites) may be selected in such manner that a major blood vessel shall lie in the light path between the first irradiation site and the detection site whereas no comparably large blood vessel shall be present in the light path between the second irradiation site and the detection site. In such a case the irradiation sites may also be equidistant from the central detection site (as shown in FIG. 10).

To make use of the effect elucidated with reference to FIGS. 9 and 10, the detection site must be located in such manner "between" the irradiation sites that it lies inside the bounding straight lines 52, 53 running perpendicularly to the connecting line 54 of the two irradiation sites 17c, 17d and through the latter. Preferably the detection site is located near the straight connecting line 54 and shall always be within a bounding circle 55 passing through both irradiation sites. Even when the measurement distances D1, D2 are unequal, the phase difference in the modulation of the primary light irradiated on the two irradiation sites 17a, 17b should be approximately 180°.

As mentioned earlier, the measurement values used in the invention for deriving the glucose concentration can be obtained by conventional measurement methods. However a number of difficult boundary conditions must be considered in the practical implementation of the invention.

First the accuracy requirements are stringent. Illustratively the phase shift between the irradiated primary light and the detected secondary light must be measured with an accuracy typically of 0.1° at a frequency in the order of 100 MHz. Using integration times of several minutes the phase angle must remain constant (free of drift) over the entire measurement time (at least several hours).

Preferably semiconductor light sources such as LEDs or laser diodes are used as light emitters. The low intensity of such primary light sources results in a very low radiation density at the light detector in the order of magnitude of nW ($10^{-9}$ watts).

The device used for the glucose analysis according to the invention should be as small compact and economical as possible. The measurement requirements therefore should be met without costly special components.

To solve the problems arising from these boundary-conditions, the invention makes use of the following additional features, which can be used individually or in combination.

Figure 11:
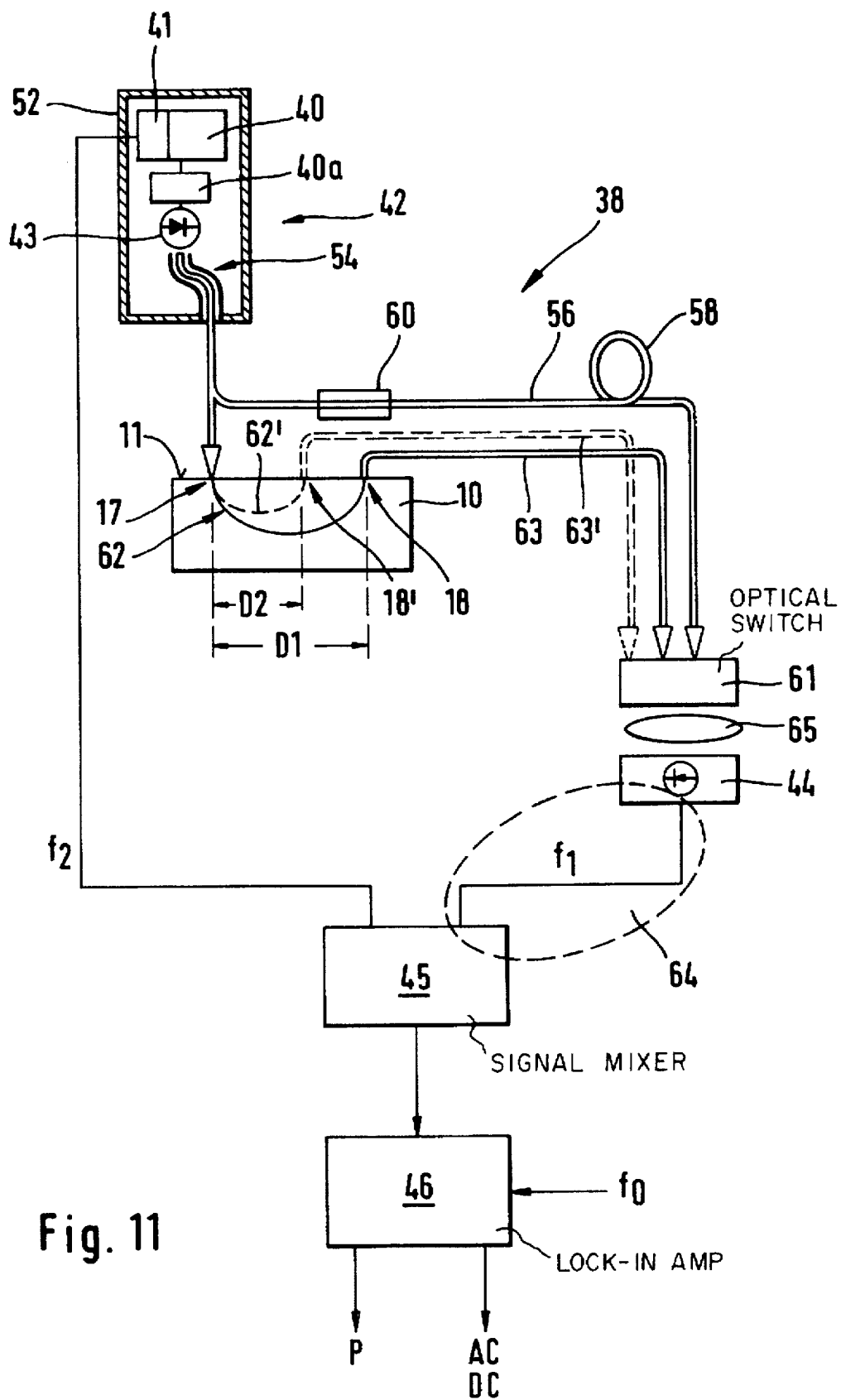
FIG. 11 is a block diagram of a further embodiment of the invention.

A first feature of the phase-measurement device 38 shown in FIG. 11 is that the two frequency generators 40, 41, the driver stage 40a and the primary light source 43 (preferably a laser diode) are arranged inside an electromagnetically insulated housing 52. The electromagnetic insulation of the housing 52 also comprises the means for leading the primary light out of the housing. The fiber-optics cable 15 passes out of the housing 52 through a duct, an electronic pitfall 54, which is essentially impermeable to electromagnetic high-frequency radiation. As a result, the high frequency power generated inside the housing 52 (which is in order of 10 mW during continuous operation and may rise to several watts in pulse operation) does not interfere with the highly sensitive phase measurement. In this regard using an electromagnetically insulating housing (for instance a completely closed metal box) to enclose the said components is highly advantageous. At least the driver stage 40a and the primary light source 43, preferably also the frequency generator 40 driving these components shall be shielded electromagnetically.

A second feature of the phase measurement device 38 which also may be advantageously used to measure other transit-time parameters is shown in FIG. 11. A reference-light path 56 is provided by which the light emitted from the primary light source 43 may be guided to the same light sensor 44 in alternative to a sample light path 63 including the measurement light path 62 through the biological matrix 10. In the shown embodiment the reference light path 56 comprises an optical delay path 58 (for instance made of fiber optics) and an optical attenuator 60. These elements are dimensioned in such manner that the reference light path 56 matches the sample light path 63, the attenuation and the delay of the light on the sample light path being determined predominantly by the measurement light path 62 within the biological matrix. The adaption of the light paths implies that both the intensity and the transit-time of the light emitted by the primary light source 43 and passing through one of the light paths 56, 63 to the light sensor 44 shall be as similar to one another as possible. Preferably the attenuation and delay in the reference light path 56 shall be set to mean values of a given measurement light path 62 occurring in practical test conditions. The corresponding deviation of the light intensity should be at most ±50%. The delay in the reference light path 56 should be matched to the delay in the sample light path 62 such that the phase shift on both paths differ at most by ±15°, preferably ±5°. According to experimental (test) results, the matching of the light paths requires a delay path 58 which is about four times the geometric distance (measurement distance) between the irradiation site 17 and the detection site 18. The delay path is defined as the difference between the length of the reference light path 56 and the length of that part of the sample light path 63 which runs outside the sample (that is, sample light path 63 minus measurement light path 62).

Using relatively simple means, the reference light path 56 may be designed to be highly stable. As a result increased sensitivity to changes in transit-time caused by changes in glucose concentration may be achieved using simple and hence economic means. In this context it is important that the sample light path 63 and the reference light path 56 can be optically switched onto the same light sensor 44. In the shown embodiment this feature is implemented by using an LCD optical switch 61 and a lens 65.

If the transit-time parameter (in particular the phase shift), and, where called for, also the AC amplitude and the DC amplitude at several different measurement distances between the irradiation site 17 and the detection site 18 shall be determined, this determination can be carried out on principle by moving the components which determine the irradiation site 17 and/or the detection site 18 along the boundary surface 11 of the biological matrix 10. A device without moving parts, however, is preferred. In FIG. 11 an embodiment is shown in dashed lines wherein a measurement distance D2 which is smaller than the measurement distance D1 and which is associated with a corresponding measurement lieght path 62' is implemented in such a way that the light emerging at the detection site 18' is directed along a further sample light path 63' (appropriately using fiber optics cable) to the same LCD optic switch 61. As a result the same phase measurement device 38 can be used to determine the measurement values, the phase difference (P), AC amplitude und DC amplitude for different measurement distance, and (if the herein discussed preferred embodiment is used) an optic reference light path 56.

A third feature of the embodiment shown in FIG. 11 is that the signal path 64 between the light sensor 44 and the signal mixer 45 is minimized. In the scope of the present invention it was found that the sensitivity of the light-detection is enhanced by this feature. A signal path which is as short as possible along the segment between the components 44 and 45 secures low line capacitance. Hence, in spite of the required high frequencies, it is possible to use a relatively high impedance of the mixer or respectively of a signal preamplifier preceding said mixer. In doing so the signal at a given current of the photodiode is increased. The effective sensitivity of the semiconduction photodetector which is simple and hence economical can therefore be substantially improved by a simple design feature.

Preferably the signal path between the light sensor 44 and the mixer 45 amounts to less than 1 cm. Especially preferred, the light sensor 44 and the signal mixer 45 are jointly integrated on the same semiconductor substrate. Several differenz circuits offer advantageous embodiments. An amplifier with a subsequent mixer, for instance a balanced mixer, may be used. An FET mixer may be used, with the light sensor 54 being directly connected to its gate. Lastly a photodiode serving as the photo-sensor may be per se a component of the mixer 45. Illustratively the photodiode may replace a diode in a balanced mixer.

Especially preferred, the light sensor 44 is an avalanche photodiode. A preferred possibility especially related to an avalanche photodiode consists in directly modulating the sensitivity of the light sensor 44 at the frequency $f_2$. In the case of a photo-multiplier, $f_2$ may be applied to its dynode in order to achieve the modulation. In the case of a semiconducting light sensor, its supply voltage may be modulated at $f_2$. As a result the functions of the light sensor 44 and of the mixer 45 are performed in combination by the same component.

Accuracy of phase measurement using a phase measurement device operating on the heterodyne principle substantially depends on the constancy of the differential frequency $f_0$ between the two frequency generators ($f_1$, $f_2$) 40 and 41 ("cross-correlation frequency") over the time of measurement. As $f_1$ (for instance 1 kHz) on the other hand only contributes a small fraction to the absolute frequencies of the frequency generators 40, 41 (for instance 100.000 MHz and 100.001 MHz), then highly stable and hence costly oscillators would be required in the frequency generators 40, 41.

Instead, in a preferred embodiment of the invention, the differential frequency $f_0$ is generated by a difference-frequency generator 66. The frequency of the second measurement-frequency generator $f_2$ is regulated on the basis of the predetermined differential frequency so that the second frequency generator 41 follows the frequency fluctuations of the first frequency generator 40 at a constant differential frequency.

Figure 12:
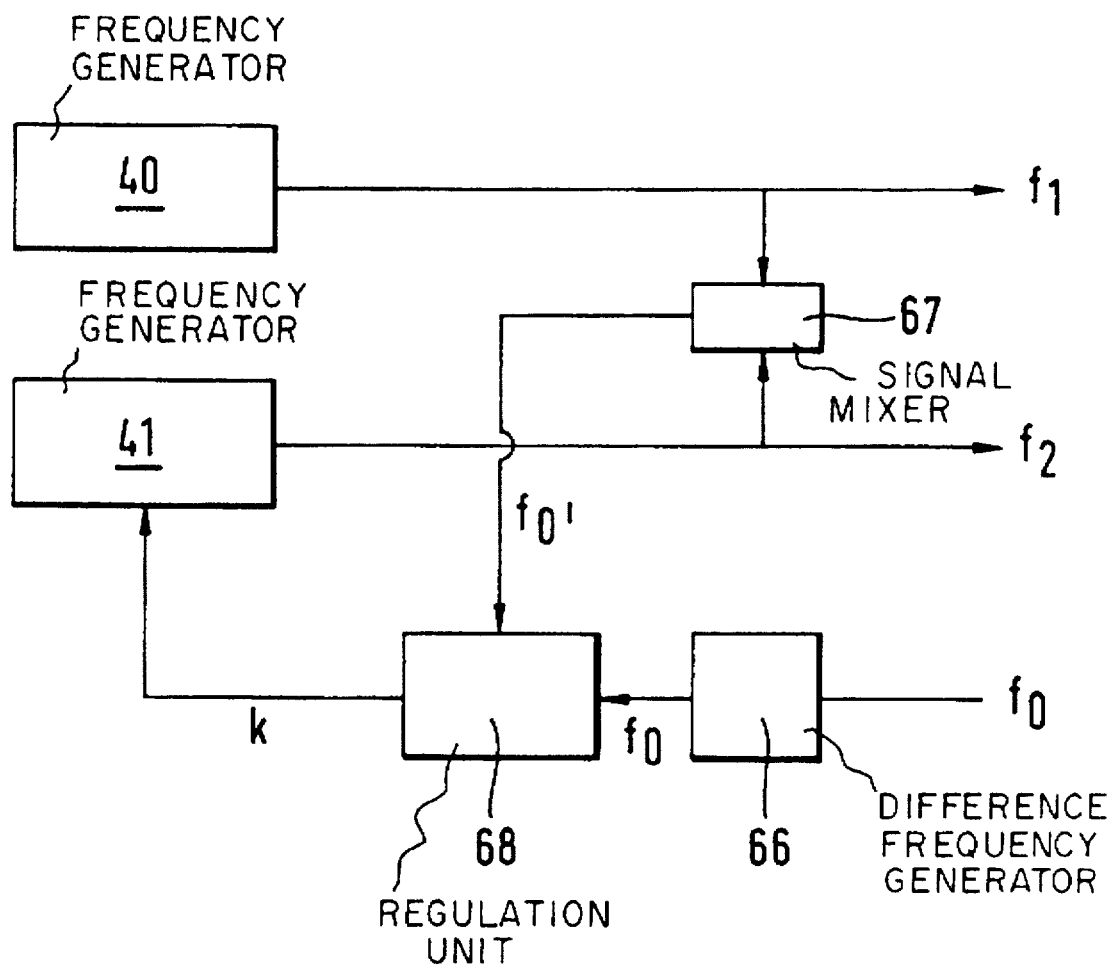
FIG. 12 is a block diagram of a preferred embodiment for frequency stabilization of two frequency generators generating a constant frequency difference.

In the embodiment according to FIG. 12 this feature is implemented in that the frequencies $f_1$ and $f_2$ of the generators 40, 41 are fed to the inputs of a signal mixer 67. The output signal thereof is the particular instantaneous differential frequency $f_0$. This differential frequency is fed as the measured actual signal to a regulation unit 68 which also receives the nominal signal in the form of the signal from the difference-frequency generator 66. The regulation unit 68 compares the actual signal $f_0$, with the nominal signal $f_0$ and generates a correction signal k which is fed to one of the two frequency generators, in FIG. 12 to frequency generator 41, in order to regulate its frequency $f_2$ so that the difference between $f_1$ and $f_2$ corresponds precisely to the predetermined differential frequency $f_0$. Preferably regulation takes place in known manner using the PLL principle.

Advantageously the particular testing techniques elucidated in relation to FIGS. 11 and 12 are also applicable to other tasks wherein the measurement values such as the phase difference P, the AC amplitude und DC amplitude, shall be measured in a scattering medium in order to determine its light propagating properties.

We claim:

1. A method of analytically determining a glucose concentration in a biological matrix, comprising the steps of:
   irradiating light from a light emitter as primary light through a boundary surface into the biological matrix;
   detecting light emerging as secondary light from said matrix through said boundary surface by a light sensor in order to determine a measurable physical property of the light that is changed by interaction with the biological matrix, said measurable physical property correlating with the glucose concentration in the biological matrix; and
   determining the glucose concentration based upon a measured change of the physical property compared to a calibration,
   wherein the measurable physical property correlating with the glucose concentration is a parameter corresponding to a light transit-time inside the biological matrix between a defined irradiation site and a defined detection site.

2. A method according to claim 1, wherein a measurement distance between the irradiation site and the detection site is less than 4 cm, preferably less than 3 cm and especially-preferred less than 2 cm.

3. A method according to claim 1, wherein the parameter corresponding to the light transit-time is determined at a plurality of different measurement distances between the irradiation site and the detection site and in that in the evaluation step a dependence of the light transit-time on the measurement distance is used to determine the glucose concentration.

4. A method according to claim 1, wherein in the detection step a short pulse of primary light is irradiated into the biological matrix and the resulting pulse emerging at the detection site is detected in order to directly determine the transit time.

5. A method according to claim 4, wherein a pulse-width of the short pulse of primary-light is less than 1 ns.

6. A method according to claim 5, wherein the pulse width is less than 100 ps.

7. A method according to claim 5, wherein the pulse width is less than 20 ps.

8. A method according to claim 1, wherein the primary light is modulated with a high-frequency carrier frequency and wherein a phase-shift of the secondary light relative to the primary light is determined as the parameter corresponding to the transit time.

9. A method according to claim 8, wherein in the detection step a change in AC amplitude of the modulation of the secondary light is determined in relation to the AC amplitude of the modulation of the primary light and said change of AC amplitude is used additionally to the phase shift in the evaluation step to determine the .glucose concentration.

10. A method according to claim 8, wherein in the detection step the change of a DC amplitude of the secondary light is determined in relation to a DC amplitude of the primary light and said change of DC amplitude is used in addition to the phase shift in the evaluation step to determine the glucose concentration.

11. A method according to claim 8, wherein the carrier frequency is higher than 50 MHz.

12. A method according to claim 11, wherein the carrier frequency is higher than 200 MHz.

13. A method according to claim 8, wherein in the at least one detection step the primary light is modulated with a plurality of different carrier frequencies and in each case a respective phase shift of the secondary light is measured relative to the primary light as a measure of a mean optical path-length.

14. A method according to claim 8, wherein in at least one detection step the primary light is simultaneously irradiated at two different irradiation sites in such manner that light intensity waves propagating from the two irradiation sites through the biological matrix are superposed and a change of light detected at a defined detection site resulting from said superposition and depending on the light transit-time between the irradiation sites and the defined detection site determines the parameter corresponding to the transit-time in the detection step and is used in the evaluation step to ascertain the glucose concentration.

15. A method according to claim 14, wherein a relative phase and a relative intensity of the primary light irradiated at the two different irradiation sites are adjusted in such manner that the change detected at the detection site with changing glucose concentration is maximized.

16. A method according to claim 11, wherein a phase of the modulation of the primary light irradiated at the two different irradiation sites differ by approximately 180°.

17. A method according to claim 14, wherein the detection site is located between two bounding straight lines each passing through one irradiation site and each perpendicular to a connecting straight line between said two irradiation sites.

18. A method according to claim 17, wherein the detection site is located within a bounding circle passing through both irradiation sites.

19. A method according to claim 14, wherein the two different irradiation sites are located at different measurement distances to the detection site.

20. A method according to claim 14, wherein the biological matrix is a tissue of a mammal, including a human, wherein one of the irradiation sites is selected in such manner that a substantial blood vessel is in the light path to the detection site, whereas the second irradiation site is selected in such a way that no comparably large blood vessel is in its light path to the detection site.

21. A method according to claim 1, wherein the wavelength of the primary light is between 400 and 2,500 nm.

22. A method according to claim 21, wherein the primary-light wavelength is between 750 and 850 nm.

23. A method according to claim 22, wherein the primary-light wavelength is between 780 and 825 nm.

24. A method according to claim 22, wherein the primary-light wavelength is between 800 and 805 nm.

25. A method according to claim 21, wherein the primary-light wavelength is between 1,150 and 1,350 nm.

26. A method according to claim 25, wherein the primary-light wavelength is between 1200 and 1300 nm.

27. A method according to claim 21, wherein the primary-light wavelength is between 1,600 and 1,800 nm.

28. A method according to claim 27, wherein the primary-light wavelength is between 1630 and 1770 nm.

29. A method according to claim 27, wherein the primary-light wavelength is between 1630 and 1670 nm.

30. A method according to claim 27, wherein the primary-light wavelength is between 1730 and 1770 nm.

31. A method according to claim 1, wherein the wavelength of the primary light is selected within a range wherein the absorption of an aqueous glucose solution presents little dependence on the glucose concentration.

32. A method according to claim 1, wherein temperature of the detection site is measured and is taken into account in the evaluation step.

33. A method according to claim 32, wherein the temperature of the detection site is measured without contact.

34. A method according to claim 1, wherein a detection-site temperature is kept constant.

35. A method according to claim 1, wherein the biological matrix is a biological liquid, in particular blood.

36. A method according to claim 1, wherein biological matrix is a biological tissue.

37. A method according to claim 36, wherein the biological matrix is skin tissue, in particular at a finger pad, an abdominal wall, a nail bed, a lip, a tongue, a human inner upper arm, or sclera tissue.

38. Apparatus for determining a glucose concentration in a biological matrix, comprising:

a measuring head to be placed against a boundary surface of the biological matrix, irradiation means with a primary light emitter for irradiating primary light through a boundary surface into the biological matrix, detection means for detecting secondary light emerging from said biological matrix through said boundary surface and for determining a physical property of the light that is changed by interaction with the biological matrix, said property correlating with the glucose concentration in the biological matrix, and evaluation means for determining the glucose concentration from the detected physical property of the light, wherein the detection means comprise means for measuring a parameter corresponding to a light transit-time along a measurement light path within the biological matrix between a defined irradiation site, and a defined detection site as a physical property of the light which correlates with the glucose concentration.

39. Apparatus according to claim 38, wherein the irradiation means comprise a measurement frequency generator and a driver stage controlling the primary light emitter thereby to modulate the primary light with a high-frequency carrier frequency, and in that the means for measuring a parameter corresponding to the light transit-time in the biological matrix comprise a phase measurement device for determining a phase shift of the secondary light relative to the primary light as a parameter correlating with the light transit-time.

40. Apparatus according to claim 39, wherein the phase-measurement device comprises means for determining an AC amplitude of the secondary light in relation to an AC amplitude of the primary light.

41. Apparatus according to claim 39, wherein the phase measurement device comprises means for determining a DC amplitude of the secondary light in relation to a DC amplitude of the primary light.

42. Apparatus according to claim 39, wherein the driver stage and the primary light emitter are enclosed in an electromagnetically insulating housing.

43. Apparatus according to claim 42, wherein the measurement frequency generator also is enclosed in an electromagnetically insulating housing.

44. Apparatus according to claim 42, wherein the phase measurement device comprises a second frequency generator which is also enclosed inside an electromagnetically insulating housing.

45. Apparatus according to claim 39, wherein the phase measurement device comprises a signal mixer receiving the output signal from a light sensor and in that the signal path between the light sensor and the signal mixer is minimized.

46. Apparatus according to claim 45, wherein the light sensor and the signal mixer are jointly integrated on the same semiconductor substrate.

47. Apparatus according to claim 46, wherein the signal mixer is a FET mixer and the light sensor is directly connected to the gate of the FET mixer.

48. Apparatus according to claim 46, wherein the light sensor is a photodiode and in that the photodiode is a part of the signal mixer.

49. Apparatus according to claim 38, wherein the means for measuring a parameter corresponding to the light transit-time along the measurement light path within the biological matrix comprise an optical reference light path which is adapted to the measurement light path regarding light transit-time and light intensity attenuation, wherein the measurement light is optically switchable between a sample light path comprising the measurement light path and the reference light path.

50. Apparatus according to claim 39, wherein the phase measurement device comprises a first and a second measuring frequency generator oscillating at a constant differential frequency wherein the differential frequency between the frequencies of the first measuring frequency generator and the second measuring frequency generator is predetermined by means of a difference-frequency generator and the frequency of the second measuring frequency generator is regulated on the basis of the predetermined differential frequency in such manner that the second measuring frequency generator follows the frequency fluctuations of the first measuring frequency generator at a constant differential frequency.

* * * * *